(12) United States Patent
Wall et al.

(10) Patent No.: US 8,453,493 B2
(45) Date of Patent: Jun. 4, 2013

(54) TRACE GAS SENSING APPARATUS AND METHODS FOR LEAK DETECTION

(75) Inventors: David Wall, Wellesley, MA (US); J. Daniel Geist, Boxborough, MA (US); Stephen M. Elliott, Longmont, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 329 days.

(21) Appl. No.: 12/917,880

(22) Filed: Nov. 2, 2010

(65) Prior Publication Data

US 2012/0103837 A1    May 3, 2012

(51) Int. Cl.
  *G01N 7/00*    (2006.01)
(52) U.S. Cl.
  USPC .......................................................... 73/31.05
(58) Field of Classification Search
  USPC ................................. 73/31.05, 40.7; 205/793
  See application file for complete search history.

(56) References Cited

U.S. PATENT DOCUMENTS

| | | | |
|---|---|---|---|
| 5,325,708 A | | 7/1994 | De Simon |
| 5,437,778 A | * | 8/1995 | Hedgcoth ................ 204/298.21 |
| 5,529,674 A | * | 6/1996 | Hedgcoth ................ 204/298.21 |
| 5,568,053 A | * | 10/1996 | Drubetsky et al. ............ 324/463 |
| 5,661,229 A | | 8/1997 | Bohm et al. |
| 6,835,048 B2 | | 12/2004 | Perkins et al. |
| 6,854,602 B2 | | 2/2005 | Oyama et al. |
| 7,204,127 B2 | | 4/2007 | Perkins et al. |
| 7,266,991 B2 | | 9/2007 | Bley |
| 7,290,439 B2 | | 11/2007 | Perkins et al. |
| 7,497,110 B2 | | 3/2009 | Liepert |

* cited by examiner

Primary Examiner — Hezron E Williams
Assistant Examiner — David Z Huang

(57) ABSTRACT

A trace gas sensing apparatus includes a cathode, an anode, a vacuum enclosure, and a membrane. The anode coaxially surrounds the cathode, wherein the cathode and the anode define an annular ionization chamber. The vacuum enclosure surrounds the cathode and the anode and includes a gas inlet fluidly communicating with the ionization chamber. The membrane is coupled to the gas inlet in a sealed manner and is permselective to trace gas. The apparatus may further include circuitry for applying a negative voltage potential to the cathode and for measuring an ion current signal generated by the cathode, and a magnet assembly for generating a magnetic field in the ionization chamber. The cathode may include an elongated member located along a longitudinal axis, and first and second end plates orthogonal to the longitudinal axis.

20 Claims, 4 Drawing Sheets

TRACE GAS SENSING APPARATUS AND METHODS FOR LEAK DETECTION

FIELD OF THE INVENTION

The present invention relates generally to detection of trace gas. More particularly, the invention relates to trace gas sensing apparatus and related components and methods for detection of trace gas.

BACKGROUND OF THE INVENTION

Trace gas leak detectors are utilized to test for leaks in various sealed components. Known leak detection systems have typically utilized a mass spectrometer to separate helium from other gas species and measure the signal. Mass spectrometers are complex and require costly components, including costly vacuum pumping systems, to sustain operation. More recently, Penning cell sensors have been employed for leak detection in response to a demand in industry for lower cost products. Systems such as described in U.S. Pat. Nos. 5,325,708; 5,661,229 and 7,266,991 utilize a Penning cell sensor to measure trace gas ion current and scale the ion current to leak rate. U.S. Pat. No. 7,497,110 describes a leak detection system utilizing a Penning cell detector combined with a composite permeable membrane of a type described in U.S. Pat. No. 6,854,602. Despite different naming conventions (e.g., ion pump, gas consuming vacuum gauge, cold cathode gauge, ionization gauge), such references describe a technology essentially based on a simple Penning cell.

FIG. 1 is a cross-sectional view of a simple Penning cell 100. The Penning cell 100 consists of a tubular anode 102 with flat cathode plates 104 at either end. A magnetic field is applied axial to the anode 102 and the anode 102 is powered at some positive voltage, typically between +3,000 and +7,000 V, resulting in a plasma with an electron trap within the interior of the anode 102. Tracer gas molecules are flowed from a test component into the Penning cell 100 and ionized in the plasma generated by the electric field applied between the anode 102 and the cathode plates 104. The resulting gas ions are accelerated toward the cathode plates 104. Electrons from the gas molecules and cathode plates 104 form a negative space-charge cloud 106 that is constrained along the central cell axis. Some electrons migrate via cross-field mobility and strike the anode 102 and this electron current is what is measured, not the actual ion current. This electron current is assumed to scale with ion current, the ion current being proportional to gas pressure. All Penning cells provide a small amount of gas pumping simultaneous with electron current measurement. When gas ions impact the cathode surface they sputter metal. The sputtered metal fragments are deposited largely on the anode surface, thereby trapping (pumping) gas ions.

All Penning cell designs suffer from several intrinsic problems that limit the sensitivity and stability of measurement in a leak detector, which include the following. The plasma in a simple Penning cell is constrained by the electric and magnetic fields inside the anode to a small ellipsoidal volume centered on the anode cell axis. The number of electrons (which sustain the plasma) and the ion current in the cell (the number of ions available for measuring) are limited by space-charge affects so leak rate sensitivity is therefore limited in a Penning cell. Further, pumping speed is directly proportional to the amount of electrons stored in the plasma. Therefore, the greater the amount of electrons stored in the plasma, the greater the pumping speed. With the plasma limited to a small volume in the center of a Penning cell, pumping speed is limited. This is a significant factor in a leak detector. The speed with which a leak detector recovers from an exposure to trace gas is highly dependent on the pumping speed of the sensor cell.

Additionally, as noted above some electrons in the trap formed by the magnetic field and the cathode plates in the Penning cell migrate via cross-field mobility to strike the anode and this is the current actually measured, not the actual ion current. In a device measuring down to $10^{-15}$ amps, this adds a significant measurement error to the leak reading. A measurement of the anode current is assumed to scale with ion current proportional to gas pressure, i.e. the number of trace gas molecules ionized. In reality, when ions impact the cathode of a Penning cell, secondary electrons are generated and scattered, many of which in turn strike the anode causing a spurious signal (since it is anode current that is actually measured). Since the secondary electron scattering is a function of several variables including the ion energy, ion mass and the angle of incidence, this adds a varying measurement error to the signal as measured in a Penning cell.

Additionally, Penning cell devices are notoriously difficult to start at very low and very high pressures. At low pressure, even though high voltage is applied the plasma may not ignite so the sensor is inoperable. There are too few gas molecules in the Penning cell to be ionized and too few electrons generated during ionization to sustain the plasma. At high pressure, the mean free path for an ion is very short so ions quickly capture a free electron and become neutralized. There are again too few ions and electrons available to sustain a plasma discharge and the sensor extinguishes. Both of these pressure conditions have resulted in operating restrictions in prior art leak detectors. For example, it is typical for the operating manual of a commercial leak detector model to specify that the unit must be started periodically and permitted to pump so that the pressure will not rise so high during storage that the sensor cannot be restarted.

Additionally, the tensile stress level in a metal thin film deposited by sputtering can be extremely high. If the film does not adhere well to the substrate, i.e. the anode surface in the present context, the film will eventually fracture and eject metal particles into the plasma. These particles may become ionized in the plasma resulting in a high current spike and the plasma will be unstable for a period of time thereafter. This appears to a leak detector user as an unstable and unacceptable variation in leak measurement. It is also well known that metals suffer from embrittlement after absorbing substantial amounts of hydrogen. As hydrogen is one of the primary gases in a permeation-based leak detector, this is a significant factor that contributes to film failure. The choice of metals used for the anode and cathode must therefore be carefully made. Titanium has historically been used in commercial devices, but this is not the best choice for a sensor that is almost exclusively exposed to helium and hydrogen. In addition, a physical geometry around the cell that encourages consistent and even metal thin film growth is a significant design consideration.

Arcing is a problem that is intrinsic to Penning cells, resulting in large ion current spikes and instability of the leak rate signal. The typical Penning cell anode is a length of thin wall tubing with sharp edges at both ends. This is true of all commercial leak detectors on the market today that utilize a Penning cell sensor. The sharp edges of the cell anode operating at potentials of several thousand volts suffer from very high field gradients at the edges, which in turn results in field breakdown and electrical arcing between the anode and other internal surfaces. Once an arc occurs and a pit with sharp protrusions is left in the metal surface, smaller arcs will occur at the pit location on an intermittent basis. Each of these arcs results in highly unstable operation of the leak detector.

Another arcing problem results from formation of columnar structures as cathode material is sputtered by the ions and a thin metal film is deposited on the anode surface. Around the edges of the anode diameter, columnar structures grow on the cathode surface having a narrow cross-section, but can reach millimeters in height. This growth is commonly referred to as "whiskers" in the industry. Consequently, Penning devices are routinely "high-potted" (subjected to very high voltages) in order to proactively burn off the whiskers. Each of these whiskers produces a significant electric field concentration pointing directly at the sharp edge of the high voltage anode tube. The high electric field concentration results in an arc and a virtual explosion of the whisker. The resulting ion current spike causes significant instability for a leak detector for some time period until the electric fields and the plasma settle again.

In a common Penning cell, erosion of the cathode plates limits lifetime. Given the shape of the plasma at the center of the anode tube, sputtering and the resulting erosion of the cathode are concentrated in a small diameter at the center of the cell. This constant erosion due to sputtering eats through the cathode material, eventually exposing the vacuum chamber wall beneath the cathode material. This of course greatly reduces pumping speed and if left to continue will eventually eat through the vacuum chamber wall creating a vacuum leak. For the type of sealed Penning cell sensors used in leak detection, this means the sensor must be discarded as the erosion pit approaches the thickness of the cathode plate, adding significant cost to maintain a leak detector.

Penning cells have low pumping speed for noble gases such as helium since noble gases do not chemically bond and cannot be getter-pumped. The primary pumping mechanism is burial by metal sputtered from the cathode onto the anode as described above. Helium, having a low mass (mass 4), has a particularly low sputtering efficiency. Once helium enters a sensor of this type, the helium is pumped away very slowly. The slow pumping results in a high background helium level, which prevents further leak testing until the background can be reduced (pumped away). In most leak test operations, time of operation is a significant cost factor and hence the time lost waiting for sensor pump out is expensive.

One of the pumping mechanisms in a Penning cell is burial of ionized gas molecules in the cathode plates. Ionized gas molecules are accelerated toward the cathode and bury themselves in the structure of the cathode material. However, because the cathode is continually being sputtered away, these gas molecules will be re-liberated over time resulting in gas bursts and ion current instability. The same gas molecules must be ionized and pumped again and again. This is especially true when pumping noble gases and extensive studies have been documented regarding noble gas instabilities in a Penning cell. An effective sensor must provide highly effective pumping of noble gases.

All of the known Penning cell-based leak detector sensors utilize a permeable membrane made from some type of quartz that must be heated to several hundred degrees Celsius in order to permeate. This requires expensive power supplies as well as control electronics in a temperature feedback control loop to ensure the temperature does not "run away". The high temperatures negatively affect both the performance and lifetime of adjacent components. It is well known in the industry that electronic components run best at the colder temperatures and fail more rapidly at high temperatures.

In view of the foregoing, there is an ongoing need for providing improved apparatus, devices and methods for leak detection, including improved sensitivity, improved stability, less complexity, and lower cost.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a trace gas sensing apparatus includes a cathode, an anode, a vacuum enclosure, and a membrane. The anode coaxially surrounds the cathode, wherein the cathode and the anode define an annular ionization chamber. The vacuum enclosure surrounds the cathode and the anode and includes a gas inlet fluidly communicating with the ionization chamber. The membrane is coupled to the gas inlet in a sealed manner. The membrane is permselective to trace gas, allowing trace gas to permeate into the gas inlet from outside the membrane but preventing permeation of atmospheric gas (e.g., oxygen, nitrogen, etc.). The apparatus also includes first circuitry configured for applying a negative voltage potential to the cathode, and second circuitry configured for measuring an ion current signal generated by the cathode.

According to another implementation, a trace gas sensing apparatus includes a cathode, an anode, a vacuum enclosure, and a membrane. The cathode includes an elongated member located along a longitudinal axis, a first end plate orthogonal to the longitudinal axis, and a second end plate orthogonal to the longitudinal axis and disposed at an axial distance from the first end plate. The anode coaxially surrounds the cathode, wherein the cathode and the anode define an annular ionization chamber. The vacuum enclosure surrounds the cathode and the anode and includes a gas inlet fluidly communicating with the ionization chamber. The membrane is coupled to the gas inlet in a sealed manner. The membrane is permselective to trace gas.

According to another implementation, a method is provided for sensing trace gas. Trace gas molecules are flowed into contact with a membrane permselective to the trace gas molecules. The trace gas molecules pass through the membrane and into a cylindrical ionization chamber, which is defined by a cathode and an anode coaxially surrounding the cathode relative to a longitudinal axis. A plasma is generated in the ionization chamber that ionizes the trace gas molecules by applying a negative voltage potential to the cathode, such that the plasma includes gas ions and electrons. The gas ions are accelerated toward and impact the cathode. A magnetic field is generated in the ionization chamber to constrain an outward radial component of trajectories of the electrons, wherein the plasma is distributed in a cylindrical volume about the longitudinal axis. An ion current signal is read. The ion current signal is produced by the cathode in response to impact by the gas ions, and is proportional to a partial pressure of the gas ions in the ionization chamber Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION OF THE INVENTION

As used herein, the term "tracer gas" or "trace gas" generally refers to helium or hydrogen, with the understanding that trace amounts of other light gases may be present with helium or hydrogen such as, for example, neon.

Figure 2:
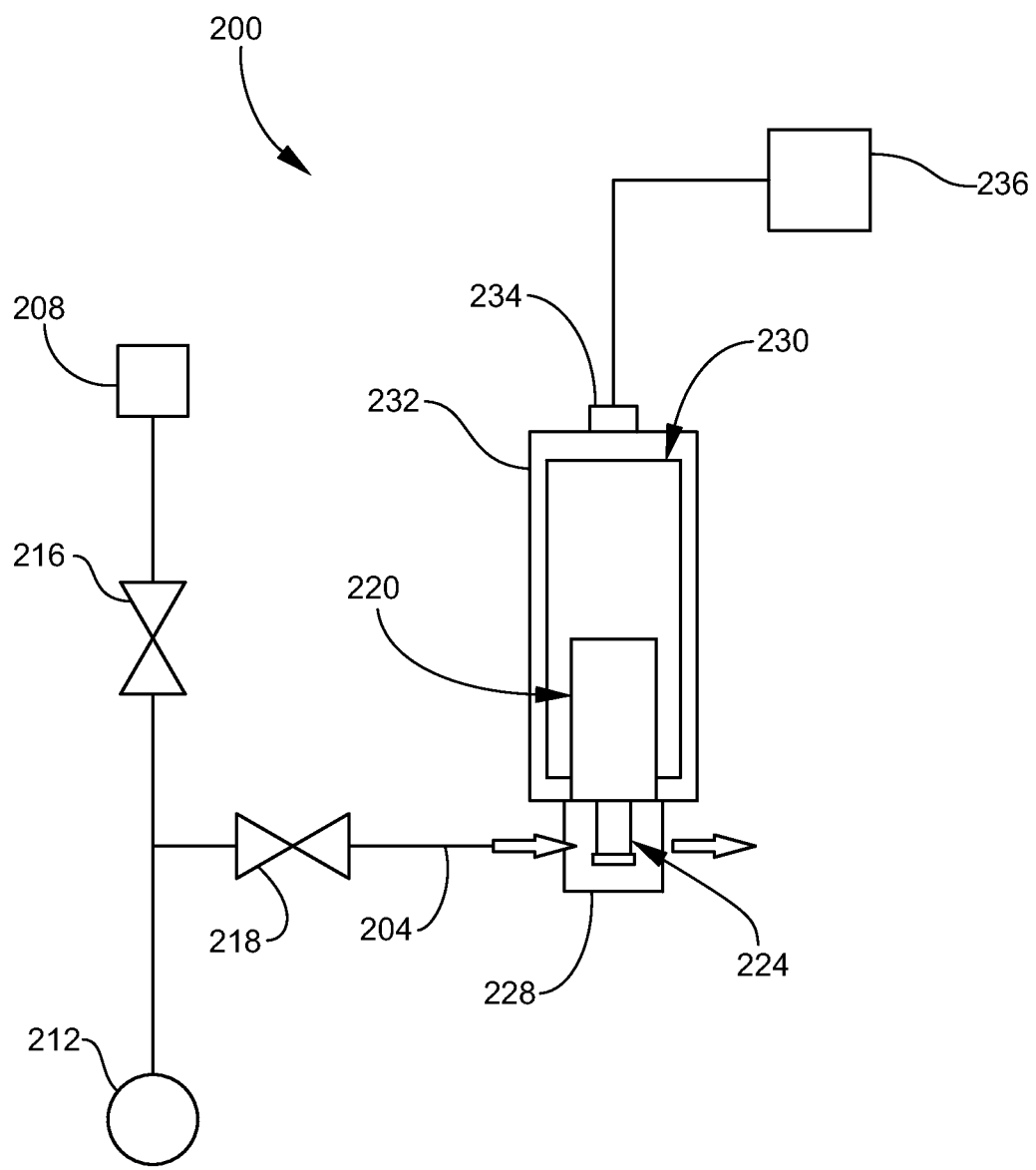
FIG. 2 is a schematic elevation view of an example of a trace gas sensing apparatus according to one implementation disclosed herein.

FIG. 2 is a schematic elevation view of an example of a trace gas sensing apparatus 200 according to one implementation disclosed herein. Generally, the trace gas sensing apparatus 200 may be or form a part of any of several types of leak detectors utilized in industry such as, for example, those based on accumulation leak testing, sniffing leak testing, or vacuum leak testing. The apparatus 200 may include a gas inlet line 204 communicating with a test component 208 (or with a sniffer probe), a vacuum pump 212, and one or more valves 216, 218 and other gas flow controllers (not shown) as needed for flowing tracer gas from the test component 208 to the apparatus 200. As appreciated by persons skilled in the art, the test component 208 may be directly connected to the gas inlet line 204 and sprayed with trace gas, or alternatively may be pressurized with trace gas after which a sniffer probe connected to the gas inlet line 204 is moved around the outside of the test component 208. The apparatus 200 includes an evacuated, plasma-based trace gas sensor cell 220 fluidly communicating with a permselective membrane 224 via a suitable vacuum-tight connection such as an interconnecting flange 228. The flange 228 interfaces with the gas inlet line 204 via any suitable means to direct the flow of tracer gas under vacuum from the test component 208 and into contact with and around the outside of the permselective membrane 224, as illustrated by arrows. Tracer gas passing through the permselective membrane 224 flows into the sensor cell 220. The sensor cell 220 is in signal communication with circuitry or electronics 230, as represented by an electronic circuit board in FIG. 2. The circuitry 230 may include a first portion (first circuitry) configured for providing power to the sensor cell 220 and a second portion (second circuitry) configured for receiving (reading, measuring, detecting, etc.) and conditioning output signals generated by sensor cell 220, which in the present implementation are ion current signals. The sensor cell 220 and circuitry 230 are enclosed in an outer housing 232. The outer housing 232 may provide an electrical connector 234 for interfacing the circuitry 230 with any additional electronics 236 that may be provided with the apparatus 200, such as hardware (e.g., an electronic processor-based controller or computer, which may execute appropriate instructions embodied in software) for deriving gas leak rate data from the ion current signals processed by the circuitry 230, a display or readout or other output interfaces, user input interfaces, memory, and other computer-related components.

Figure 3:
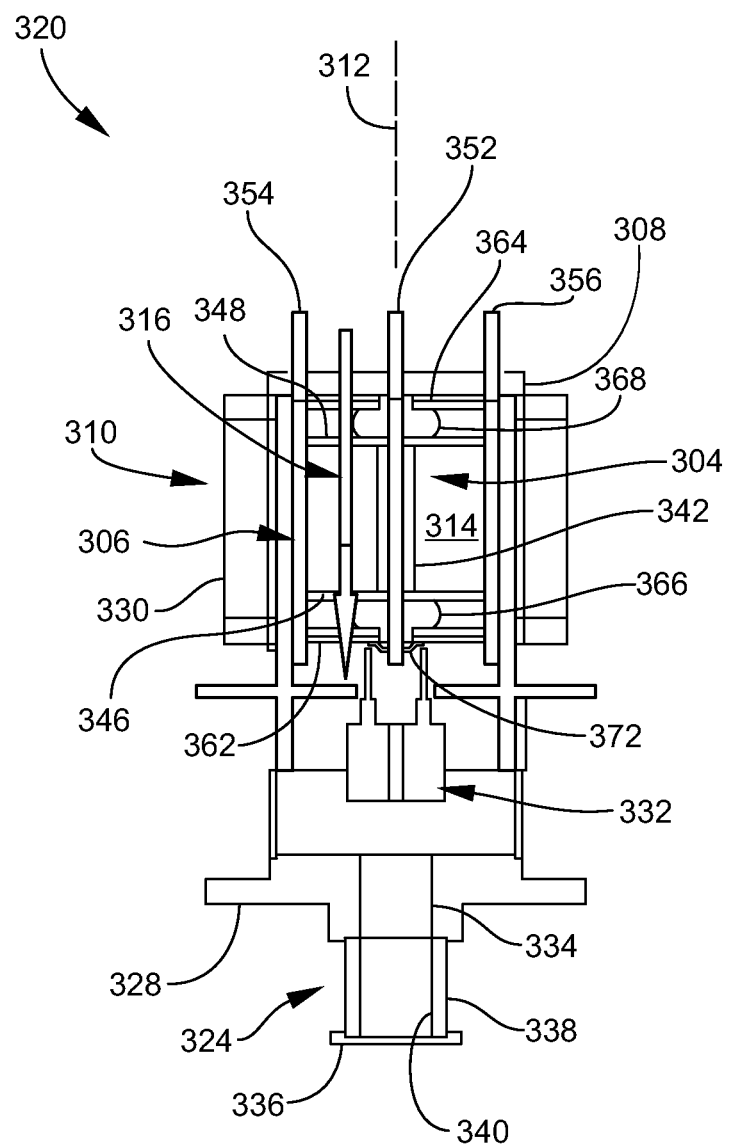
FIG. 3 is a cross-sectional view of an example of a trace gas sensor cell according to one implementation disclosed herein.

FIG. 3 is a cross-sectional view of an example of a trace gas sensor cell (or sensor cell assembly) 320 according to one implementation. The sensor cell 320 may be provided in a trace gas sensing apparatus such as described above and illustrated in FIG. 2, and thus may correspond to the sensor cell 220 illustrated in FIG. 2. The sensor cell 320 generally includes a cathode 304, an anode 306, a vacuum enclosure or housing 308 enclosing the cathode 304 and anode 306, a magnet assembly 310, and a permselective membrane 324. The vacuum enclosure 308 is generally any structure capable of being evacuated and maintained at a desired level of vacuum. The vacuum enclosure 308 includes one or more structural members (walls, seals, etc.) as needed for enclosing the cathode 304 and anode 306 and supporting other components of the sensor cell 320. The vacuum enclosure 308 may be composed of any metal, glass or ceramic that is vacuum compatible. In the present implementation, the cathode 304 and the anode 306 are disposed along a longitudinal axis 312. The cathode 304 is centrally located such that at least a portion of the cathode 304 is disposed along the longitudinal axis 312. The anode 306 coaxially surrounds the cathode 304 relative to the longitudinal axis 312. The cathode 304 and anode 306 cooperatively define a space that may be characterized as an ionization chamber or plasma chamber 314. The permselective membrane 324 is attached to the vacuum enclosure 308 in a vacuum-sealed manner such that the sensor cell 320 establishes a flow path for trace gas molecules from the permselective membrane 324, through a portion of the vacuum housing 308, and into the ionization chamber 314. The magnet assembly 310 is configured for establishing a magnetic field in the ionization chamber 314 to constrain the radial motions of electrons. The magnetic field is schematically represented by a vector 316 in FIG. 3.

When configured for utilizing helium as the tracer gas, the sensor apparatus 320 may include a getter pump 332 interposed in the gas flow path between the permselective membrane 324 and the ionization chamber 314. In some implementations, the getter pump 332 is a non-evaporable getter (NEG) pump. The getter pump 332 may be configured for removing hydrogen in a manner appreciated by persons skilled in the art, and may be a commercially available getter pump Accordingly, the getter pump 332 may be configured to have a very large pumping speed for hydrogen so as to remove virtually all hydrogen from the vacuum space. By this configuration, the helium partial pressure is directly proportional to system leak rate. In other implementations in which the sensor apparatus 320 is configured for measuring hydrogen tracer gas, the getter pump 332 may be removed from the sensor cell 320.

In the present example, the permselective membrane 324 is disposed at an axial end of the vacuum housing 308 and coupled to the vacuum housing 308 by an interconnecting flange 328 through which is formed a gas inlet 334 communicating with the permselective membrane 324. In the present example, the permselective membrane 324 is cylindrical and aligned with the gas inlet 334 along the longitudinal axis 312. One axial end of the permselective membrane 324 is coupled to the interconnecting flange 328 at the gas inlet 334, and an opposing axial end of the permselective membrane 324 is sealed (covered) with a metal cap 336. The permselective membrane 324 is adjoined to the interconnecting flange 328 and the metal cap 336 is adjoined to the permselective membrane 324 in a vacuum-tight manner by any suitable means such as, for example, application of an epoxy. As an alternative to a cylinder the permselective membrane 324 may be planar, such as a plate or window that covers (spans) the gas inlet 334 of the interconnecting flange 328. However, the cylindrical geometry of the permselective membrane 324 illustrated in FIG. 3 provides a large surface area to which the incoming stream of tracer gas may be exposed.

In some implementations, the permselective membrane 324 is configured to have a high permeate selectivity (permselectivity) for helium and hydrogen and a high permeance for helium and hydrogen in a temperature range around ambient. The permselective membrane 324 substantially blocks other gas species—that is, only helium and hydrogen permeate the permselective membrane 324 in meaningful (non-negligible) quantities. The permselective membrane 324 may be further configured to exhibit a net permeance that is substantially constant and independent of temperature within a design temperature range of, for example, 0° C. to 100° C. By this configuration, the permselective membrane 324 does not require heating to a high temperature in order to initiate permeation, which is a significant factor in the design of a practical and stable leak detection sensing unit. In some implementations, these properties may be achieved by providing the permselective membrane 324 as a composite membrane that includes two or more membrane layers. As one non-limiting example, the permselective membrane 324 includes a base (first) layer or substrate 338 structured as a porous membrane, and a second layer 340 structured as a semi-permeable membrane. The porosity of the composite may be graded from a relatively large porosity in the first layer 338 to a relatively small porosity in the second layer 340, with the second layer 340 determining the permeance of the overall composite structure. Depending on the compositions of the first layer 338 and the second layer 340, the second layer 340 may be deposited as a thin film on the first layer 338 by a suitable vacuum deposition technique such as chemical vapor deposition (CVD), although other techniques may be suitable such as thermal evaporation, sol-gel deposition, spray coating, etc. The layers of the composite may be, for example, ceramics such as alumina ($Al_2O_3$), silica ($SiO_2$) or titania ($TiO_2$), quartz, quartz glass, borosilicate glass, or permeable polymers such as, for example, tetrafluoroethylene or fluoropolymers thereof (polytetrafluoroethylene or PTFE, such as TEFLON®), fluoropolymers (e.g., ethylene tetrafluoroethylene or ETFE), a copolymer of hexafluoropropylene and tetrafluoroethylene (e.g., fluorinated ethylene propylene or FEP), polyimides such as poly(4,4'-oxydiphenylene-pyromellitimide) (e.g., KAPTON®), polyethylene terephthalate such as biaxially-oriented polyethylene terephthalate (e.g., PET, such as MYLAR®), acedtate, polyamide, etc. In one specific example, the first layer 338 is alumina and the second layer 340 is silica. The permselective membrane 324 may be of the types described in U.S. Pat. Nos. 6,854,602 and 7,497,110, the contents of both of which are incorporated by reference herein in their entireties.

In general operation, tracer gas molecules permeate the permselective membrane 324, enter the vacuum enclosure 308 and flow into the ionization chamber 314. If helium is to be measured, the getter pump 332 is included and operated to remove any hydrogen molecules. A fixed electric field is generated in the ionization chamber 314 by impressing a voltage potential between the cathode 304 and the anode 306, and a fixed magnetic field is generated in the ionization chamber 314 by the magnet assembly 310. The electric field ionizes the gas molecules, thereby generating a plasma comprising positively charged gas ions and electrons. The motions of the electrons are constrained (trapped) in radial directions by the magnetic field, and in axial directions by end plates 346 and 348. The gas ions are strongly attracted to the cathode 304 and thus accelerate toward and impact the cathode 304. Collision of the gas ions with the cathode 304 generates a current in the cathode 304. This ion current is outputted as a signal to circuitry 230 (FIG. 2) for processing and conditioning to calculate tracer gas leak rate. Collision of the gas ions with the cathode 304 also sputters the cathode 304. The sputtered fragments of cathode material are transported through the plasma and are deposited as a thin film on the inside surface of the anode 306. This physical vapor deposition process has the effect of burying gas ions (and fast neutral species) beneath the as-deposited film, thereby removing (i.e., "pumping") the gas ions from the ionization chamber 314.

In some advantageous implementations, the cathode 304 is centrally located in the ionization chamber 314, such as by including an axial central portion and opposing axial end portions separated by an axial distance along the longitudinal axis 312. For example, the cathode 304 may be spool-shaped. The spool-shaped configuration is realized in the illustrated example by providing the cathode 304 in the form of an axially elongated member, post, rod, etc. (or central member, or central cathode portion) 342 collinear with the longitudinal axis 312, a first end plate 346 located at or near an axial end of the elongated member 342, and a second end plate 348 located at or near an opposite axial end of the elongated member 342 at an axial distance from the first end plate 346. The first end plate 346 and the second end plate 348 may be oriented in a transverse (or radial) plane orthogonal to the longitudinal axis 312. The first end plate 346 and the second end plate 348 may be integrally formed with the elongated member 342 or joined to the elongated member 342 by any suitable means. In typical implementations, the elongated member 342 is cylindrical and the end plates 346, 348 are circular.

The anode 306 in this example is generally cylindrical. In the present context, the term "generally cylindrical" refers to a configuration in which the anode 306 includes a wall coaxial with the longitudinal axis 312 at a radial distance therefrom, and extending for an axial length in parallel with the longitudinal axis 312. The term "generally cylindrical" also encompasses implementations in which the anode 306 has the shape of a basic cylinder such as shown in FIG. 3, as well as other implementations in which the anode 306 is overall shaped as a cylinder but may include additional geometric or structural features that modify the basic cylindrical shape to provide an advantage, such as improving the uniformity of the electrical field in the ionization chamber 314. The anode 306 may coaxially surround the cathode 304, including the end plates 346, 348. Accordingly, the ionization chamber 314 may generally be bounded in radial directions by the inside surface of the anode 306 and the outside surface of the elongated member 342, and in axial directions by the end plates 346, 348. The ionization chamber 314 may thus be characterized as being annular or cylindrical about the longitudinal axis 312. The outside diameters of the end plates 346, 348 are less than the inside diameter of the anode 306 such that respective annular gaps exist between the end plates 346, 348 and the anode 306 along the transverse plane. Gas molecules passing through the permselective membrane 324 may flow into the ionization chamber 314 via the annular gap formed between the first end plate 346 and the anode 306. Alternatively, the first end plate 346 may also have perforations or apertures (not shown) providing inlets for gas molecules into the ionization chamber 314.

A voltage source (or means for providing a voltage potential) may be placed in signal communication with the cathode 304 by any suitable means to provide a negative voltage potential to the cathode 304. Such a voltage source is schematically represented by the circuitry 230 depicted in FIG. 2. The voltage potential may range, for example, from −2,000 to −9,000 V. In one specific example, the voltage potential is −3,000 V or thereabouts. In the illustrated example, the voltage source electrically communicates with the cathode 304 via a metal electrode (e.g., pin) 352 having a feed-through design (i.e., a powered feed-through electrode) that extends through the vacuum enclosure 308 in a sealed manner. A portion of or the entire elongated member 342 may be hollow, and one or both end plates 346, 348 may have a central bore, such that the powered feed-through electrode 352 extends through part or all of the axial length of the cathode 304, thus enabling the sensor cell 320 to make a direct measurement of the ion current. The powered feed-through electrode 352 may also be utilized to output the ion current signal to the ion current measuring portion of the circuitry 230. Alternatively, a separate feed-through electrode (not shown) may be provided for outputting the ion current signal to the ion current measuring portion of the circuitry 230. The powered feed-through electrode 352 may also serve a secondary function of supporting the cathode 304 and other components. In some implementations, the anode 306 is maintained in an electrical ground state. The anode 306 may be grounded by any suitable means. In the illustrated example, the anode 306 electrically communicates with one or more grounded feed-through electrodes (e.g., pins) 354, 356, which may also serve a secondary function of supporting the anode 306 and/or other components.

In the present example, the magnet assembly 310 includes a cylindrical magnet 330 coaxially surrounding the anode 306. Typically, the magnet 330 is a permanent magnet but in other implementations may be an electromagnet. The cylindrical magnet 330 may be disposed in the vacuum enclosure 308 or, as illustrated in FIG. 3, outside the vacuum enclosure 308. Due to its geometry and orientation, the cylindrical magnet 330 establishes a magnetic field parallel to the central cathode axis (longitudinal axis 312). The magnetic field strength at the center of the sensor cell 320 may range, for example, from a few hundred G (gauss) to several thousand G. In another non-limiting example, the field strength ranges from 300 G to 7,000 G. In another example, the field strength is 1030 G or thereabouts. The magnet assembly 310 may also include a first end cap 342 and a second end cap 344 positioned at opposing axial ends of the sensor cell 320. The end caps 362, 364 serve as magnetizable pole pieces shaped and positioned to optimize the magnetic field for maximum ion formation and sensitivity. In the illustrated example, the end caps 362, 364 are plate-shaped structures positioned in parallel with the respective end plates 346, 348 of the cathode 304. The first end cap 362 is positioned at an axial distance from the first end plate 346 in an axial direction away from the ionization chamber 314, and the second end cap 364 is positioned at an axial distance from the second end plate 348 in an opposite axial direction away from the ionization chamber 314. The powered feed-through electrode 352 may pass through one or both end caps 362, 364. The respective end caps 362, 364 may be electrically isolated from the end plates 346, 348 by insulators 366, 368 composed of a suitable insulating or dielectric material such as glass. In the illustrated example, respective toroidal insulators 366, 368 are interposed between the end caps 362, 364 and the end plates 346, 348. The insulators 366, 368 may be supported by the powered feed-through electrode 352. The elongated member 342 and end plates 346, 348 of the cathode 304 and the end caps 362, 364 of the magnet assembly 310 may be stacked or otherwise assembled together by any suitable means. In the illustrated example, the powered feed-through electrode 352 passes through the end caps 362, 364 and the cathode 304, and these components are pressed together and held in place against an upper section of the vacuum enclosure 308 by flexible washers 372 attached to an end of the powered feed-through electrode 352 and positioned in biasing contact with the first end cap 362.

As noted above, when gas ions impact the cathode 304, metal particles are ejected (sputtered) and form a metal film on the anode surface, thereby trapping tracer gas molecules in the film. The physical geometry and electric field geometry inside the sensor cell 320 may be designed to create a large ion formation zone and a high level of sputtering to produce a continuous metal film in which to efficiently bury (pump) helium atoms, as well as sufficient surface area on which to efficiently trap this gas. In addition to the geometry of the cathode 304 and anode 306, the respective metals of the cathode 304 and anode 306 should be selected to ensure the sputter-deposition of a robust, continuous film on the anode surface effective for burying low-mass tracer gas species without subsequent delaminating of the film and release of buried species. Thus, the anode 306 may be composed of any metal that bonds well to the sputtered cathode material, minimizes the risk of fracturing of the sputtered metal film, and is non-magnetic. In some implementations, the anode 306 may be composed of stainless steel having a non-magnetic alloy composition. Other examples of suitable compositions for the anode 306 include, but are not limited to, aluminum, copper, and titanium. The cathode 304 (elongated member 342 and end plates 346 and 348) should generally be composed of a fairly high-mass or dense metal effective for trapping low-mass gas species and which reliably and repeatably forms a film on an anode surface of a given composition (e.g., non-magnetic stainless steel) under the operating parameters (partial pressure, temperature, electrical and magnetic field parameters, etc.) contemplated during operation of the sensor cell 320. In some implementations, the cathode 304 may be composed of molybdenum (Mo), tantalum (Ta), or titanium (Ti). The combination of a molybdenum cathode 304 and a stainless steel anode 306 has been found to work well in several of the implementations disclosed herein. Molybdenum has a good sputtering yield and vacuum properties and adheres well to stainless steel, thereby minimizing film failure and the attendant sensor instabilities described earlier in this disclosure. Moreover, molybdenum is a very dense metal with a high molecular mass, and thus sputtered molybdenum particles effectively cover and trap gas molecules. The high mass is particularly significant for pumping helium tracer gas. Titanium (Ti) has conventionally been employed for Penning cell cathodes because it readily getters gas molecules. However, because helium is an inert gas that does not bond chemically and cannot be getter-pumped, the mass of the sputtered material is a far more significant factor in effective pumping of helium for a trace gas leak detection sensor. The only way to "pump" helium is by physically trapping it in the sputtered metal film on the anode surface. Molybdenum readily covers and traps helium in the sputtered film and being so massive, it does not easily release the trapped helium when an ion impact occurs that disrupts the anode surface. Not re-evolving helium from the anode surface, preventing periodic gas bursts, and not needing to pump the same gas molecules many times over are significant advantages over conventional sensor cells and enable rapid recovery from a trace gas exposure.

As shown in FIG. 3, the upper and lower edges (i.e., axially opposite first and second anode ends of the cylindrical body) of the anode 306 may be axially positioned well above and below the end plates 346, 348 of the cathode 304. Stated in another way, the axial length of the anode 306 is greater than the axial length of the cathode 304 and the cathode 304 is positioned within the confines of the anode 306, such that one axial end of the anode 306 is axially spaced from the first end plate 346 of the cathode 304 in a direction away from ionization chamber 314 and the other axial end of the anode 306 is axially spaced from the second end plate 348 in an opposite direction away from the ionization chamber 314. This configuration ensures highly uniform electric fields in the region of the ionization chamber 314 between the end plates 346, 348 because fringe field effects and perturbations caused by the edges of the anode 306 are distanced from the ionization chamber 314, which reduces the propensity for electrical arcing between the anode 306 and the cathode 304.

It may be beneficial to "peen" the metal film being sputtered on the anode surface as peening will assist in forming a dense film that adheres well to the anode 306 and resists fracture and consequent particle ejection into the plasma. In some implementations, the anode 306 may be biased negative with respect to the cathode 304 and to ground potential, such that ions can bombard the anode surface creating a denser and more stable deposited film. For this purpose, a voltage source (or means for providing a voltage potential) may be placed in signal communication with the anode 306 by any suitable means to provide a positive voltage potential to the anode 306. Such a voltage source is schematically represented by the circuitry 230 depicted in FIG. 2. The voltage potential may range, for example, from −50 to −100 V. The negative bias voltage will attract positive helium ions and enhance bombardment of the anode surface by positive ion species thereby peening the film.

The geometry of the spool-shaped cathode 304 as described above helps to create an electric field that captures a large number of ions and electrons in a cylindrical volume around the elongated member 342 of the cathode 304. Electrons orbit around the elongated member 342 in cycloidal trajectories and are also constrained by the negatively charged end plates 346, 348 of the cathode 304. Hence, the electrons attain extremely long path lengths in the sensor cell 320. This results in a high probability of electrons striking and ionizing gas molecules in the sensor cell 320, which in turn yields a large number of ions and electrons and a correspondingly large plasma volume. The resulting large, dense ion cloud yields more ions available for measurement as compared to a Penning cell and thereby results in much greater sensitivity. In some implementations, the sensitivity of the sensor cell 320 disclosed herein is up to ten times greater than the sensitivity of a Penning cell. Moreover, as pumping speed is directly related to ion cloud volume, the large cylindrical ion cloud volume yields a greater pumping speed than a Penning cell. As noted earlier in this disclosure, both of these factors are significant for response to a leak signal and fast recovery after a large tracer gas exposure. The ion cloud has a volume (or spatial distribution) that is annular (i.e., cylindrical) about the longitudinal axis 312 and occupies the majority (e.g., 60 to 80%) of the volume of the ionization chamber 314.

In some implementations, all corners and edges of the cathode 304 are well-rounded to optimize the electric fields inside the sensor cell 320 and prevent localized, high-strength field concentrations that would cause the field emissions and arcing commonly occurring in a Penning cell as noted earlier in this disclosure. Moreover, the geometry of the cathode 304 and the presence of the end plates 346, 348 prevent the formation of whiskers and the associated arcing and instability observed in Penning cells.

The central cathode design in conjunction with applied negative voltage potential provides advantages for reading tracer gas ion current. Nearly all tracer gas molecules that enter the sensing cell 320 through the permselective membrane 324 are ionized and constrained in the electric and magnetic fields established in the ionization chamber 314, thereby creating a plasma. Tracer gas ions, being positively charged, are accelerated to and impact the cathode 304. The ion current reading is directly proportional to the partial pressure of the tracer gas and thereby gives a direct measurement of the leak rate, as opposed to an indirect measurement by way of measuring electron current as is done in a Penning cell. That direct measurement of ions at the cathode 304 yields a more precise and stable measurement of ion current as compared to a Penning cell, which in turn results in a more accurate and repeatable leak rate measurement from the presently disclosed sensor cell 320.

Figure 1:
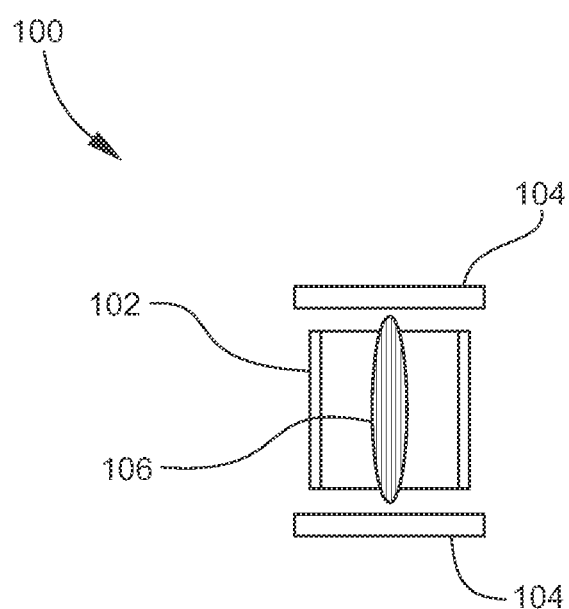
FIG. 1 is a cross-sectional view of a simple Penning cell known in the art.

In a conventional Penning cell, the positively charged anode drives positive ions toward the grounded cathode, but because the electron cloud and electric field are concentrated at the cell axis (see FIG. 1) sputtering is concentrated to a couple of square millimeters of the cathode near the cell axis. The resulting cathode erosion pattern localized at the cell axis is well known in the industry. By contrast, the cathode 304 of the present disclosure is located in the center of the sensor cell 320 such that the electron cloud is distributed evenly around the cathode 304. The negatively charged cathode 304 of the present disclosure readily attracts ions to a large fraction of the cathode surface. Most of the entire cathode surface of several square centimeters is therefore available for sputtering, which may provide two significant benefits for good performance of a leak detector sensor. First, the erosion lifetime of the sensor is increased many times as compared to Penning cells. The sputtering is not concentrated in a small area that can rapidly eat through the cathode 304 to the underlying vacuum enclosure 308, as in the case of a Penning cell. Instead, the cathode 304 of the present disclosure presents a large surface for sputtering that is an order of magnitude (or more than one order of magnitude) larger than that of a Penning cell. In addition, the sheer volume of cathode material available for sputtering is also an order of magnitude (or more) larger, so cathode erosion lifetime is much longer as compared to a Penning type sensor. This is a significant cost-of-ownership factor in the leak detection industry. Second, the cathode geometry of the present disclosure encloses the anode 306 on three sides of a square. As seen from the two-dimensional perspective of FIG. 3, the cathode 304 presents three surfaces to the anode 306—the central elongated member 342 and the two end plates 346 and 348, which form a three-sided U-shape with the open end of the "U" facing the anode 306. Because the sputtered film evolves from a large area of the cathode surface and the cathode metal is sputtered in a cosine distribution from each ion impact site, the resulting film deposited on the anode surface is uniform and even over the entire anode surface, which results in excellent film properties for good adhesion. In addition, the central elongated member 342 may be provided as a cylindrical structure, which provides more opportunity for ions to impact this portion of the cathode 304 at small angles of incidence, thereby improving sputtering.

In addition, metal thin films tend to grow in low density columnar structures from random initiation sites. If the anode 306 of the present disclosure is negatively biased, ions can strike the anode surface, which has the effect in thin film deposition of "peening" the metal film as it is growing. This peening mechanism helps to achieve a dense and more uniform film with superior adherence. This good film quality leads directly to stable and highly sensitive operation of the sensor. Additionally, because the cathode 304 erodes at such a slow rate, any gas molecules that have been embedded in the cathode sub-surface will remain trapped (pumped) and not evolve rapidly as gas background, as occurs in a Penning cell. Furthermore, the geometric configuration of the sensor cell 320 of the present disclosure is superior to Penning cells for starting at low vacuum pressure. The order-of-magnitude larger plasma volume and ion cloud ensure there are sufficient ions and electrons to sustain the plasma down to ultra-high vacuum pressure levels.

Figure 4:
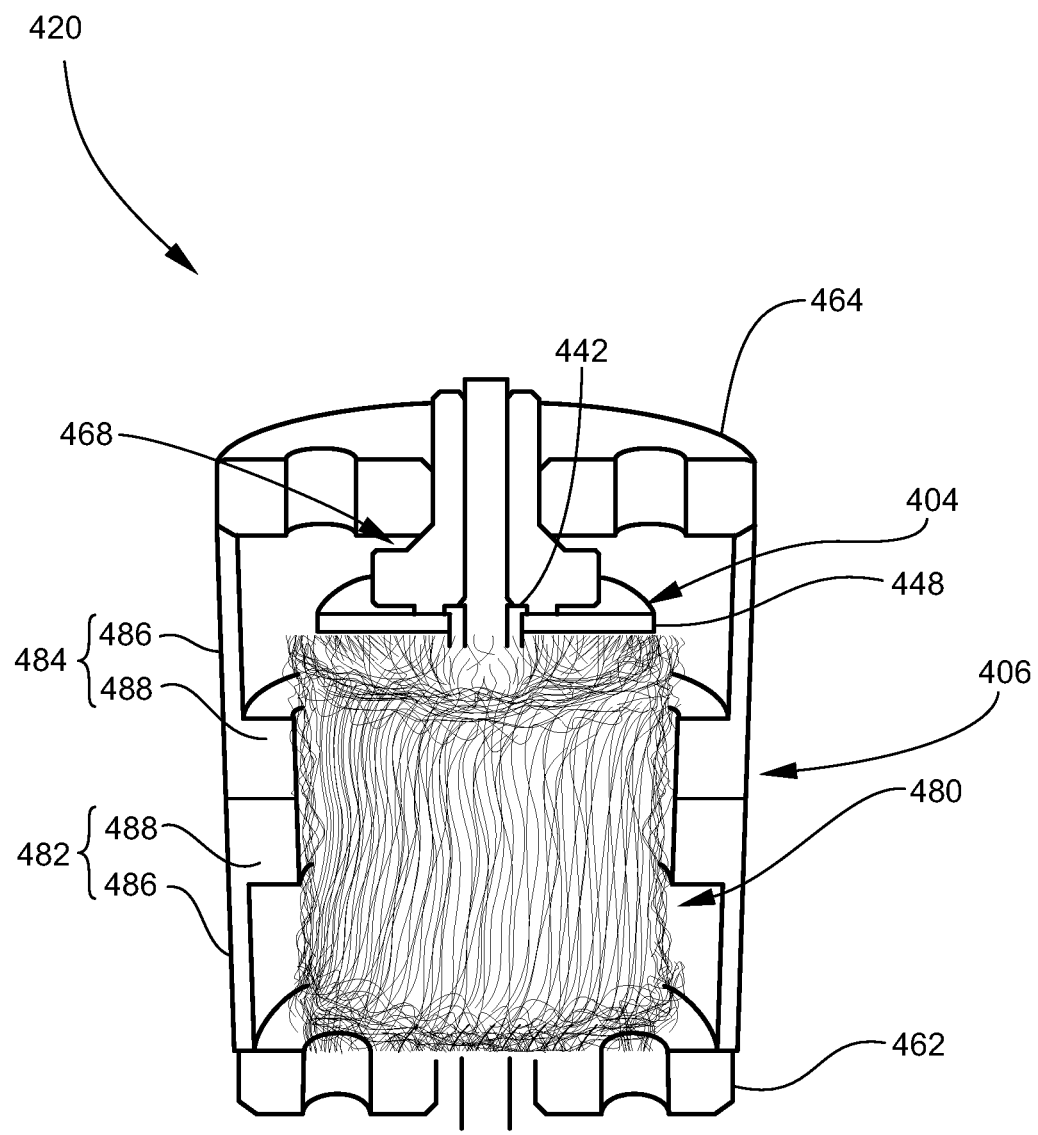
FIG. 4 is a cross-sectional view of an example of a sensor cell according to another implementation of the present teachings, rendered by computer simulation.

As noted above, the anode 306 may be a simple cylinder as shown in FIG. 3, or it may be "shaped" to further optimize the electric field and ion formation zone. One example of a modified cylindrical shape is shown in FIG. 4, which is a cross-sectional view of an example of a sensor cell 420 according to another implementation of the present teachings, rendered by computer simulation. The sensor cell 420 includes a cathode 404 with a central elongated member 442 and axial end plates 448, a generally cylindrical anode 406, and end caps 462, 464 of a magnet assembly isolated from the cathode 404 by glass insulators 468. Ion and electron motion was simulated, resulting in a large, cylindrical plasma volume 480. The anode 406 may include a plurality of physically distinct regions or sections. In the illustrated example, the anode 406 includes two cylindrical anode sections 482, 484 positioned in series along the axis of the sensor cell 420. The anode sections 482, 484 may be integrated as part of a single-piece construction of the anode 406, or alternatively may be physically separate sections. Each anode section 482, 484 includes a first portion (large-diameter portion) 486 and a second portion (small-diameter or reduced-diameter portion) 488 of lesser inside diameter than the first portion 486. The respective second portions 488 are adjacent to each other and located in a central location along the axial length of the anode 406. More generally, the respective second portions 488 are closer to each other than to either axial end of the anode 406. The second portions 488 extend inward along a radial direction toward the axis of the sensor cell 420, and may be characterized as rings or ribs integral with the respective first portions 486. The anode 406 in this example may be characterized as including at least one reduced-diameter section (the second portions 488 in FIG. 4) axially interposed between two larger-diameter sections (the first portions 486), i.e., between a first larger-diameter section on one side of the reduced-diameter section and a second larger-diameter section on the other side of the reduced-diameter section.

From the foregoing description, it can be seen that the geometry of the cathodes and anodes as taught herein may be implemented to generate optimized electric field lines, which results in maximizing electron trapping, ionization efficiency, and area available for sputter erosion. Optimized field lines increase the containment of the electrons and help to spread out the volume of the electron cloud so that the electrons have a higher probability of ionizing gas molecules. The greater spatial distribution of the electrons also spreads out the ions so that the ions impact a larger area of the cathode. The spool-shaped cathode in conjunction with the generally cylindrical anode assists in achieving maximized electron trapping, ionization efficiency, and area available for sputter erosion. Modifications to the cylindrical anode, such as illustrated in FIG. 4, may be implemented to further shape the field lines and improve electron trapping, ionization efficiency, and area available for sputter erosion.

In general, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A trace gas sensing apparatus, comprising:
a cathode;
an anode coaxially surrounding the cathode, wherein the cathode and the anode define an annular ionization chamber;
first circuitry configured for applying a negative voltage potential to the cathode;
second circuitry configured for measuring an ion current signal generated by the cathode;
a magnet assembly configured for generating a magnetic field in the ionization chamber;
a vacuum enclosure surrounding the cathode and the anode and comprising a gas inlet fluidly communicating with the ionization chamber; and
a membrane permselective to trace gas, the membrane sealing the gas inlet and configured for allowing trace gas to permeate into the gas inlet from outside the membrane.

2. The trace gas sensing apparatus of claim 1, wherein the cathode comprises an elongated member located along a longitudinal axis, a first end plate orthogonal to the longitudinal axis, and a second end plate orthogonal to the longitudinal axis and disposed at an axial distance from the first end plate.

3. The trace gas sensing apparatus of claim 1, comprising a getter pump interposed between the gas inlet and the ionization chamber.

4. The trace gas sensing apparatus of claim 1, wherein the first circuitry is configured for applying a negative voltage potential ranging from −2,000 to −9,000 volts.

5. The trace gas sensing apparatus of claim 1, comprising a ground electrode communicating with the anode.

6. The trace gas sensing apparatus of claim 1, wherein the cathode has a composition selected from the group consisting of molybdenum, tantalum, and titanium.

7. The trace gas sensing apparatus of claim 6, wherein the anode has a non-magnetic composition selected from the group consisting of non-magnetic stainless steel, aluminum, copper, and titanium.

8. The trace gas sensing apparatus of claim 1, wherein the membrane is configured to exhibit a substantially constant permselectivity to trace gas over a temperature range from 0 to 100° C.

9. The trace gas sensing apparatus of claim 1, wherein the membrane is cylindrical.

10. The trace gas sensing apparatus of claim 1, wherein the membrane comprises a plurality of layers, the plurality of layers comprising at least a porous layer and a semi-permeable layer disposed on the porous layer.

11. The trace gas sensing apparatus of claim 1, comprising a voltage source configured for applying a negative voltage bias to the anode.

12. A trace gas sensing apparatus, comprising:
a cathode comprising an elongated member located along a longitudinal axis, a first end plate orthogonal to the longitudinal axis, and a second end plate orthogonal to the longitudinal axis and disposed at an axial distance from the first end plate;

an anode coaxially surrounding the cathode, wherein the cathode and the anode define an annular ionization chamber;

a vacuum enclosure enclosing the cathode and the anode and comprising a gas inlet fluidly communicating with the ionization chamber; and a membrane permselective to trace gas, the membrane sealing the gas inlet and configured for allowing trace gas to permeate into the gas inlet from outside the membrane.

13. The trace gas sensing apparatus of claim 12, comprising a magnet assembly configured for generating a magnetic field in the ionization chamber, the magnet assembly comprising a cylindrical magnet surrounding the ionization chamber, a first end cap orthogonal to the longitudinal axis and axially spaced from the first end plate, and a second end cap orthogonal to the longitudinal axis and axially spaced from the second end plate.

14. The trace gas sensing apparatus of claim 13, comprising a first insulator axially interposed between the first end cap and the first end plate, and a second insulator axially interposed between the second end cap and the second end plate.

15. The trace gas sensing apparatus of claim 12, wherein the elongated member comprises a hollow portion, and further comprising an electrode extending through the vacuum enclosure and into the hollow portion in signal communication with the elongated member.

16. The trace gas sensing apparatus of claim 12, wherein the anode comprises a first anode end axially spaced from the first end plate in a direction away from the ionization chamber, and a second anode end axially spaced from the second end plate in an opposite direction away from the ionization chamber.

17. The trace gas sensing apparatus of claim 12, wherein the anode comprises a first large-diameter section, a second large-diameter section, and a reduced-diameter section axially interposed between the first large-diameter section and the large-diameter section.

18. A method for sensing trace gas, the method comprising:

flowing trace gas molecules into contact with a membrane permselective to the trace gas molecules, wherein the trace gas molecules pass through the membrane and into a cylindrical ionization chamber, the ionization chamber defined by a cathode and an anode coaxially surrounding the cathode relative to a longitudinal axis;

generating a plasma in the ionization chamber that ionizes the trace gas molecules, by applying a negative voltage potential to the cathode, wherein the plasma comprises gas ions and electrons and the gas ions are accelerated toward and impact the cathode;

generating a magnetic field in the ionization chamber to constrain an outward radial component of trajectories of the electrons, wherein the plasma is distributed in a cylindrical volume about the longitudinal axis; and reading an ion current signal produced by the cathode in response to impact by the gas ions, the ion current proportional to a partial pressure of the gas ions in the ionization chamber.

19. The method of claim 18, wherein reading comprises outputting the ion current signal through an electrode extending through a vacuum housing enclosing the anode and the cathode and in signal communication with a portion of the cathode positioned along the longitudinal axis.

20. The method of claim 18, wherein the ions impacting the cathode sputter fragments of cathode material from the cathode, and comprising promoting deposition of a film of the sputtered fragments on a surface of the anode such that gas species become embedded in the film, and promoting peening of the as-deposited film by additional gas ion species, by maintaining the anode at a negative voltage potential.

* * * * *

US008453493C1

(12) EX PARTE REEXAMINATION CERTIFICATE (10881st)
United States Patent
Wall et al.

(10) Number: US 8,453,493 C1
(45) Certificate Issued: Jun. 9, 2016

(54) TRACE GAS SENSING APPARATUS AND METHODS FOR LEAK DETECTION

(75) Inventors: David Wall, Wellesley, MA (US); Daniel Geist, Boxborough, MA (US); Stephen M. Elliott, Longmont, CO (US)

(73) Assignee: AGILENT TECHNOLOGIES, INC., Loveland, CO (US)

Reexamination Request:
No. 90/013,475, Mar. 26, 2015

Reexamination Certificate for:
Patent No.: 8,453,493
Issued: Jun. 4, 2013
Appl. No.: 12/917,880
Filed: Nov. 2, 2010

(51) Int. Cl.
*G01N 7/00* (2006.01)
*G01N 27/62* (2006.01)

(52) U.S. Cl.
CPC ...................................... *G01N 27/62* (2013.01)

(58) Field of Classification Search
None
See application file for complete search history.

(56) References Cited

To view the complete listing of prior art documents cited during the proceeding for Reexamination Control Number 90/013,475, please refer to the USPTO's public Patent Application Information Retrieval (PAIR) system under the Display References tab.

*Primary Examiner* — Anjan Deb

(57) ABSTRACT

A trace gas sensing apparatus includes a cathode, an anode, a vacuum enclosure, and a membrane. The anode coaxially surrounds the cathode, wherein the cathode and the anode define an annular ionization chamber. The vacuum enclosure surrounds the cathode and the anode and includes a gas inlet fluidly communicating with the ionization chamber. The membrane is coupled to the gas inlet in a sealed manner and is permselective to trace gas. The apparatus may further include circuitry for applying a negative voltage potential to the cathode and for measuring an ion current signal generated by the cathode, and a magnet assembly for generating a magnetic field in the ionization chamber. The cathode may include an elongated member located along a longitudinal axis, and first and second end plates orthogonal to the longitudinal axis.

At the time of issuance and publication of this certificate, the patent remains subject to pending reissue application number 14/731,152 filed Jun. 4, 2015. The claim content of the patent may be subsequently revised if a reissue patent is issued from the reissue application.

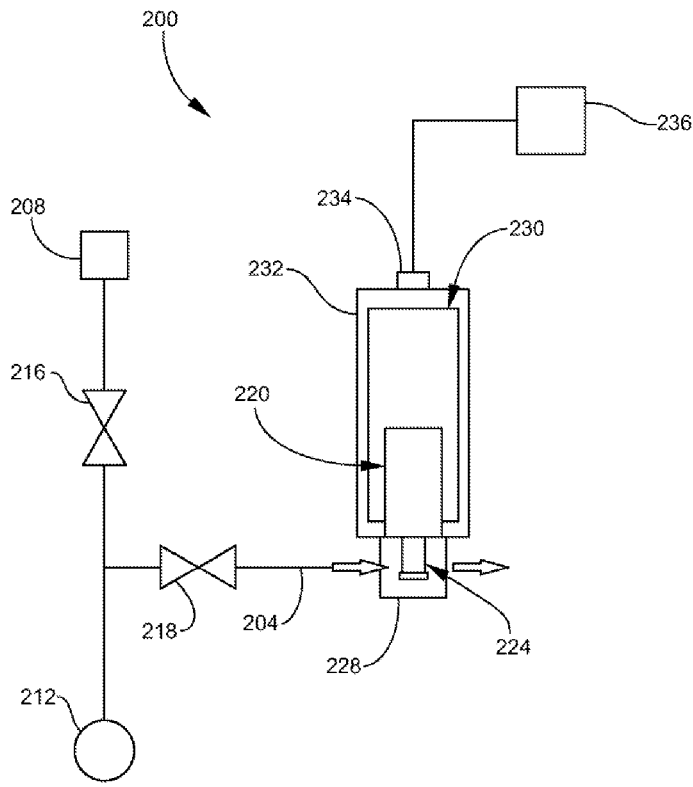

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 12 is confirmed.

Claim 2 is cancelled.

Claims 1 and 18 are determined to be patentable as amended.

Claims 3-6, 10 and 19, dependent on an amended claim, are determined to be patentable.

Claims 7-9, 11, 13-17 and 20 were not reexamined.

1. A trace, gas sensing apparatus comprising:
a cathode, *wherein the cathode comprises an elongated member located along a longitudinal axis, a first end plate orthogonal to the longitudinal axis, and a second end plate orthogonal to the longitudinal axis and disposed at an axial distance from the first end plate*;
an anode coaxially surrounding the cathode, wherein the cathode and the anode define an annular ionization chamber;
first circuitry configured for applying a negative voltage potential to the cathode;
second circuitry configured for measuring an ion current signal generated by the cathode;
a magnet assembly configured for generating a magnetic field in the ionization chamber;
a vacuum enclosure surrounding the cathode and the anode and comprising a gas inlet fluidly communicating with the ionization chamber; and
a membrane permselective to trace gas, the membrane sealing the gas inlet and configured for allowing trace gas to permeate into the gas inlet from outside the membrane.

18. A method for sensing trace gas, the method comprising:
flowing trace gas molecules into contact with a membrane permselective to the trace gas molecules, wherein the trace gas molecules pass through the membrane and into a cylindrical ionization chamber, the ionization chamber defined by a cathode and an anode coaxially surrounding the cathode relative to a longitudinal axis, *wherein the cathode comprises an elongated member located along a longitudinal axis, a first end plate orthogonal to the longitudinal axis, and a second end plate orthogonal to the longitudinal axis and disposed at an axial distance from the first end plate*;
generating a plasma in the ionization chamber that ionizes the trace gas molecules, by applying a negative voltage potential to the cathode, wherein the plasma comprises gas ions and electrons and the gas ions are accelerated toward and impact the cathode;
generating a magnetic field in the ionization chamber to constrain an outward radial component of trajectories of the electrons, wherein the plasma is distributed in a cylindrical volume about the longitudinal axis; and
reading an ion current signal produced by the cathode in response to impact by the gas ions, the ion current proportional to a partial pressure of the gas ions in the ionization chamber.

* * * * *